(12) United States Patent
Mondello et al.

(10) Patent No.: US 12,041,163 B2
(45) Date of Patent: *Jul. 16, 2024

(54) SECURE MEDICAL APPARATUS COMMUNICATION

(71) Applicant: Micron Technology, Inc., Boise, ID (US)

(72) Inventors: Antonino Mondello, Messina (IT); Alberto Troia, Munich (DE)

(73) Assignee: Micron Technology, Inc., Boise, ID (US)

( * ) Notice: Subject to any disclaimer, the term of this patent is extended or adjusted under 35 U.S.C. 154(b) by 16 days.

This patent is subject to a terminal disclaimer.

(21) Appl. No.: 17/862,396

(22) Filed: Jul. 11, 2022

(65) Prior Publication Data

US 2022/0353064 A1  Nov. 3, 2022

Related U.S. Application Data

(63) Continuation of application No. 16/362,890, filed on Mar. 25, 2019, now Pat. No. 11,387,983.

(51) Int. Cl.
*H04L 9/08* (2006.01)
*G16H 40/67* (2018.01)
(Continued)

(52) U.S. Cl.
CPC ........... *H04L 9/0825* (2013.01); *G16H 40/67* (2018.01); *H04L 9/3247* (2013.01);
(Continued)

(58) Field of Classification Search
CPC ... H04L 9/0825; H04L 9/3247; H04L 9/3263; H04L 63/0442; G16H 40/67
See application file for complete search history.

(56) References Cited

U.S. PATENT DOCUMENTS 9,980,140 B1   5/2018  Spencer et al.
11,218,330 B2 * 1/2022  Mondello ........... H04L 63/0823
(Continued)

FOREIGN PATENT DOCUMENTS

EP   3016011 A1   5/2016
EP   3821561      5/2021
(Continued)

OTHER PUBLICATIONS

England et al., (RioT A Foundation for Trust in the Internet of Things, Microsoft, 2016, 17 pages), (Year: 2016).*
(Continued)

*Primary Examiner* — Oleg Korsak
(74) *Attorney, Agent, or Firm* — Brooks, Cameron & Huebsch, PLLC

(57) ABSTRACT

Secure medical apparatus communication is described herein. An example apparatus can include a processor and an apparatus communication component. The apparatus communication component can be coupled to the processor and can be configured to, in response to receiving data from an external communication component, generate an apparatus private key and an apparatus public key, provide the apparatus public key and data to the external communication component, receive data from the external communication component in response to providing the apparatus public key and data to the external communication component, decrypt the received data using the apparatus private key, verify an identity of the external communication component, and in response to verifying the identity of the external communication component, perform an operation on the medical apparatus using the received data.

20 Claims, 8 Drawing Sheets

(51) Int. Cl.
*H04L 9/32* (2006.01)
*H04L 9/40* (2022.01)

(52) U.S. Cl.
CPC ........ *H04L 9/3263* (2013.01); *H04L 63/0442* (2013.01); *H04L 2209/805* (2013.01); *H04L 2209/88* (2013.01)

(56) References Cited

U.S. PATENT DOCUMENTS

| | | | |
|---|---|---|---|
| 11,387,983 B2* | 7/2022 | Mondello | H04W 12/033 |
| 2008/0103554 A1 | 5/2008 | Dicks et al. | |
| 2012/0088983 A1 | 4/2012 | Jung et al. | |
| 2014/0321648 A1 | 10/2014 | Kim | |
| 2015/0207626 A1 | 7/2015 | Neftel et al. | |
| 2017/0259072 A1 | 9/2017 | Newham et al. | |
| 2017/0279602 A1 | 9/2017 | Pham | |
| 2018/0182487 A1 | 6/2018 | Kullik et al. | |
| 2018/0316505 A1 | 11/2018 | Cohen et al. | |
| 2019/0036688 A1 | 1/2019 | Wasily et al. | |
| 2019/0036886 A1 | 1/2019 | Wu et al. | |
| 2020/0021431 A1* | 1/2020 | Mondello | H04W 12/041 |
| 2020/0021981 A1* | 1/2020 | Mondello | H04W 12/03 |

FOREIGN PATENT DOCUMENTS

| | | |
|---|---|---|
| KR | 10-2012-0036244 A | 4/2012 |
| KR | 10-2012-0068827 A | 6/2012 |
| WO | 2018-112035 A1 | 6/2018 |

OTHER PUBLICATIONS

U.S. Appl. No. 15/853,498, entitled, "Physical Unclonable Function Using Message Authentication Code", filed Dec. 22, 2017, 28 pages.
U.S. Appl. No. 16/201,652, entitled, "Parking Infrastructure Powered By a Decentralized, Distributed Database", filed Nov. 27, 2018, 27 pages.
U.S. Appl. No. 15/993,119, entitled, "Transmission of Vehicle Route Information By Passive Devices", filed May 30, 2018, 25 pages.
U.S. Appl. No. 16/034,763, entitled, "Secure Vehicular Communication", filed Jul. 13, 2018, 37 pages.
U.S. Appl. No. 16/034,809, entitled, "Secure Vehicular Services Communication", filed Jul. 13, 2018, 36 pages.
PCT International Application No. PCT/IB2019/000089, entitled, "Method for Improving Safety of a Component or System Running a Firmware or a Finite State Machine", filed Feb. 22, 2019, 42 pages.
International Search Report and Written Opinion from related International Application No. PCT/US2020/024375, dated Jul. 17, 2020, 10 pages.
Mattoon, Denis, "Implementing DICE", Trusted Computing Group, Mar. 20, 2018, found on website: develop.trustedcomputinggroup.org/2018/03/20/implementing-dice/, Accessed May 7, 2020.
Alfred J. Menezes, et al., "Handbook of Applied Cryptography", CRC Press, Aug. 1996, 88 pages.

* cited by examiner

SECURE MEDICAL APPARATUS COMMUNICATION

PRIORITY INFORMATION

This application is a Continuation of U.S. application Ser. No. 16/362,890, filed on Mar. 25, 2019, the contents of which are incorporated herein by reference.

TECHNICAL FIELD

The present disclosure relates generally to apparatuses and methods related to medical apparatuses, and more particularly, to secure medical apparatus communication.

BACKGROUND

Medical apparatuses and devices (e.g., medical prosthesis apparatuses) can communicate with scanners, servers, wireless devices, etc. to obtain and exchange information. The medical apparatuses can be implanted into a patient in order to affect biological and/or additional functioning of the patient. Over time, a patient's needs or the affect of the medical apparatus on the patient can change. In order to avoid adverse affects of the medical apparatus on the patient, for example, the medical apparatus can be updated in order to improve operational efficiency, more closely match with a patient's needs or recommendations of a physician by communication with an external device.

DETAILED DESCRIPTION

Figure 1:
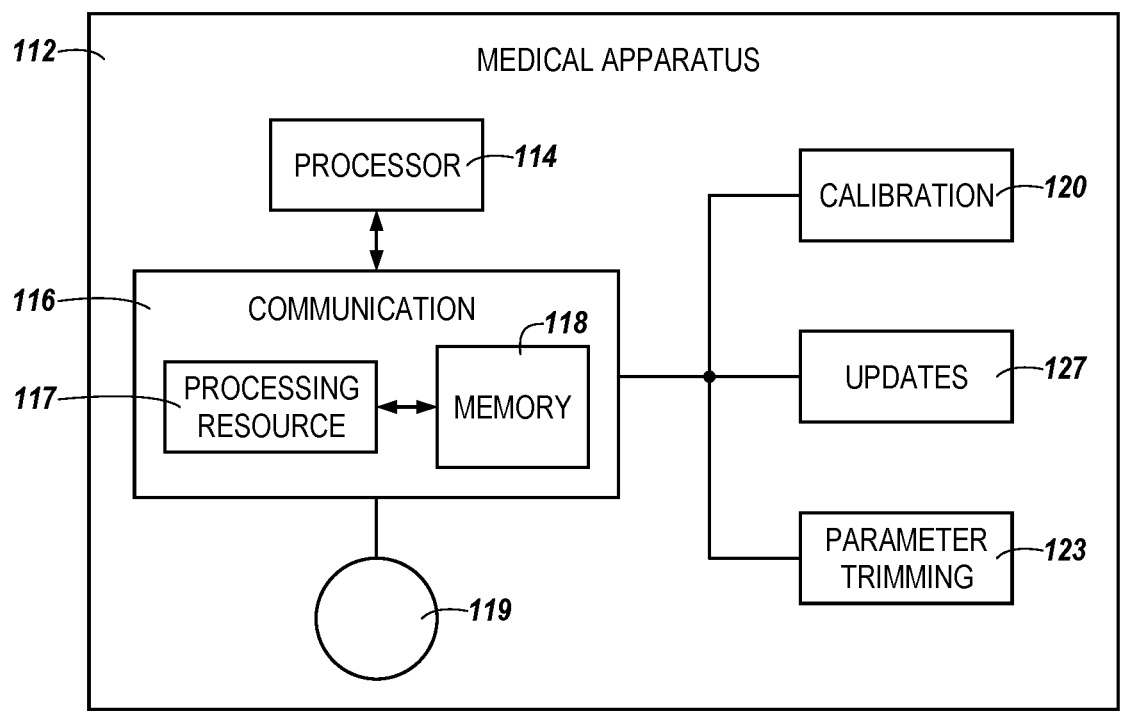
FIG. 1 is a block diagram of an example medical apparatus, in accordance with an embodiment of the present disclosure.

Secure medical apparatus communication is described herein. An example medical apparatus can include a processor and an apparatus communication component. The apparatus communication component can be coupled to the processor and can be configured to generate an apparatus private key and an apparatus public key, provide the apparatus public key and data to an external communication component associated with a medical apparatus, receive data from the external communication component in response to providing the apparatus public key and data to the external communication component, decrypt the received data using the apparatus private key, verify an identity of the external communication component, and, in response to verifying the identity of the external communication component, perform an operation on the medical apparatus using the received data.

In some previous approaches, a medical apparatus can communicate with external devices (e.g., scanner devices) without secure communication. The communication between the medical apparatus and the external devices may be intercepted and/or manipulated by a hacker or other entities in order to change the communication, repeat the communication to gain unauthorized access to the medical apparatus, etc. In such instances, the medical apparatus may not use identification of the external device to verify that the communication is authorized prior to gaining access to the medical apparatus. This unauthorized communication can provide updates that may negatively affect the medical apparatus or a patient using the medical apparatus or that the medical apparatus is implanted within.

Apparatus communication components can provide medical data and/or updates that can improve the operation of the medical apparatus, resulting in technological improvements to the medical apparatus and better patient outcomes. For example, information provided by the apparatus communication components can be used to update the medical apparatus, fine-tune operation of the medical apparatus to tailor its operation to a particular patient based on the patient's medical data, etc. However, in these previous approaches, the communication between the medical apparatus and the external device can be both public and unsecured. In addition, the communication may not be able to be verified, introducing possible nefarious activity that can negatively affect the performance of the medical apparatus.

As will be described herein, by introducing a secure form of communication for providing medical data, updates, etc, and an ability to accurately identify who is requesting and/or receiving the medical data (e.g., medical information), information related to nefarious activity in relation to the medical apparatus can be rejected, avoided, discarded, etc. Public keys can be exchanged and used to encrypt data while private keys, which remain private and exclusive to a single entity, can be used to decrypt data. In this way, those without the private key are prevented from intercepting service data and using it for purposes other than initially intended. Further, certificates and signatures can be used to verify identities of a sender of medical data and insure that data originates from an intended source.

FIG. 1 is a block diagram of an example medical apparatus 112 in accordance with an embodiment of the present disclosure. As shown, the medical apparatus 112 can include a processor 114 coupled to an apparatus communication component 116, such as a reader, writer, and/or other computing device capable of performing the functions described below, that is coupled to (e.g., or includes) an antenna 119.

Apparatus communication component 116 can include a processing resource 117 coupled to a memory 118, such as a non-volatile flash memory, although embodiments are not so limited. The medical apparatus 112 can be within and/or implanted within a patient, a medical device, a medical system, etc.

Medical apparatus 112 can control operational parameters such as calibration, updates, and/or parameter trimming, among other criteria not illustrated. For example, a controller (not shown) can be coupled to a calibration system 120, an update system 127, and a parameter trimming system 123. The calibration system 120 can be used to calibrate the medical apparatus 112, e.g., based on a change in a status of a patient associated with the medical apparatus 112, a change in medical information related to the patient, a change in treatment status, etc. The update system 127 can be used in collaboration with the calibration system 120 to provide the calibration system 120 updated information in order to further calibrate the medical apparatus 112. The parameter trimming system 123 can be used to trim a parameter associated with the medical apparatus 112, such as a frequency, an intensity, etc., of a setting of a device, e.g., of an electrical stimulation in a pacemaker, among other medical parameters depending on which type of medical apparatus and/or medical device is being used.

Figure 2:
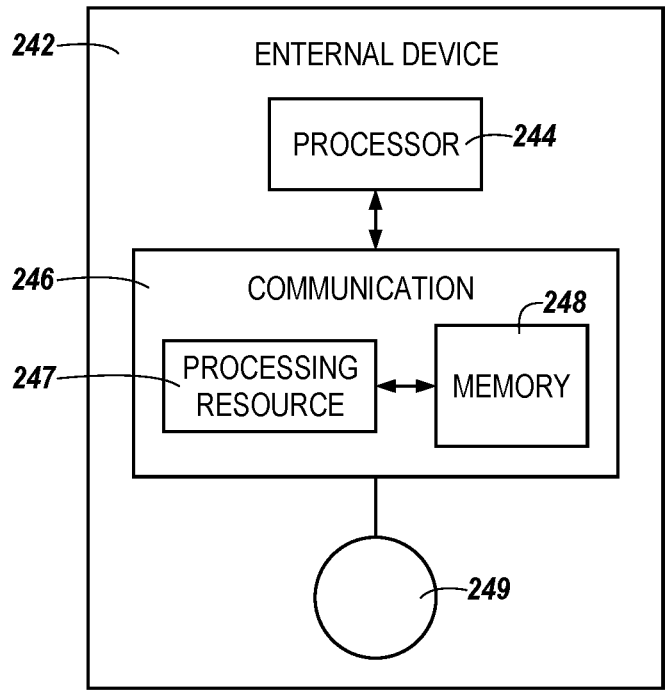
FIG. 2 is a block diagram of an example external device in accordance with an embodiment of the present disclosure.
Figure 3:
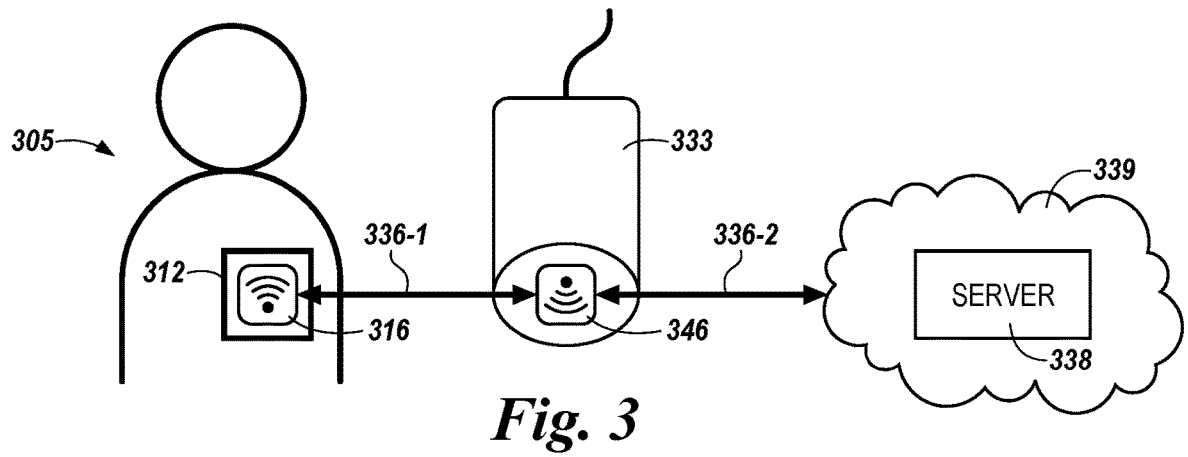
FIG. 3 is an example environment, including a medical apparatus, an external device, and a server device, in accordance with an embodiment of the present disclosure.

Apparatus communication component 116 can receive medical data from additional computing devices, such as an external device (e.g., a scanner device) 242 described in association with FIG. 2, or a server system (such as server system 338 as described in FIG. 3). Processor 114 can execute instructions to cause calibration system 120 to adjust a medical parameter of the medical apparatus 112 and/or parameter trimming system 123 to trim a parameter of the medical apparatus 112 in response (e.g., according) to the medical data from external communication component 246 in FIG. 2. In some examples, the parameter can be one of a frequency, a phase of an oscillation, an amplitude, other service parameters to optimize the medical apparatus functionality, such as firmware parameters to respond better to a patient's heart rate (in the case of a pacemaker). As a further example, other applications can decide how much insulin to provide and at which rate, based on a continuous measurement of the medical apparatus. In addition, for example, the medical data can be received to indicate a change in a parameter of a patient, a change in the treatment for the patient, etc. In some examples, the apparatus communication component 116 can be coupled to a heart apparatus, a blood apparatus, a pulse apparatus, a prosthetic apparatus, a bone-inserted apparatus, an insulin measurement system, a position system, an electronic body part (i.e., a hand, a leg, and/or anything able to retrieve data and having an ability to send data out of the body).

FIG. 2 is a block diagram of an external device 242, such as a remote medical device that can communicatively couple to the medical device shown in FIG. 1. In one example, the external device 242 may be a remote scanner device. The external device 242 can be a computing device used to scan the medical apparatus 112 in FIG. 1. The external device 242 can use various communication methods, such as wireless communication, to communicate with the medical apparatus 112. In the example of FIG. 2, the external device 242 can include a processor 244 to execute instructions and control functions of the external device 242. The processor 244 may be coupled to an external communication component 246, such as a reader, writer, transceiver, and/or other computing device or circuitry capable of performing the functions described below to exchange information, that is coupled to (e.g., or includes) an antenna 249. External communication component 246 can include a processing resource 247 coupled to a memory 248, such as a non-volatile flash memory, although embodiments are not so limited. The antenna 249 of the external device 242 can be in communication with, e.g., communicatively coupled to, the antenna 119 of the medical apparatus 112 shown in FIG. 1.

In some examples, antennas 249 and 119 can be loop antennas configured as inductor coils, etc. Antenna 119 can loop around medical apparatus 112, for example. Antenna 119 can generate an electromagnetic field in response to current flowing through antenna 119. For example, the strength of the electromagnetic field can depend on the number of coils and the amount of current. The electromagnetic field generated by antenna 119 can induce current flow in an antenna 249 that powers the respective external device 242. As an example, antenna 119 in FIG. 1 can induce current flow in antenna 249 when the external device 242 is brought within a communication distance (e.g., a communication range) of the antenna 119. For example, the communication distance can depend on the strength of the electromagnetic field generated by antenna 119. The electromagnetic field generated by antenna 119 can be set, by the number of coils of antenna 119 and/or the current passing through antenna 119, such that the communication distance can span from the location of the internal placement of the medical apparatus 112 within a patient to the external device 242 outside the patient. In some examples, the communication distance can be about 50 centimeters to about 100 centimeters on either side of medical apparatus 112. In the alternative, the communication distance can depend on the strength of the electromagnetic field generated by antenna 249. In this instance, the electromagnetic field generated by antenna 249 can be set by the number of coils of 249 and/or the current passing through antenna 249.

In some examples, the external device 242 can include a number of wireless communication devices, such as transmitters, transponders, transceivers, or the like. As an example, the external communication component 246 can be such a wireless communication device. Wireless communication that can be used can include near field communication (NFC) tags, RFID tags, or the like. In at least one embodiment, wireless communication can be performed using non-volatile storage components that can be respectively integrated into chips, such as microchips. Each of the respective chips can be coupled to a respective antenna, such as antenna 249. The respective storage components can store respective medical data.

Medical data can be transmitted from the apparatus communication component 116 of the medical apparatus 112 to the external communication component 246 of the external device 242 in response to the medical apparatus 112 passing within the communication distance of the respective external device 242. The medical data can be transmitted in the form of signals, such as radio frequency signals. For example, the apparatus communication component 116 of the medical apparatus 112 and the external communication component 246 of the external device 242 can communicate using radio frequency signals.

For examples in which wireless communication devices are NFC tags, apparatus communication component 116 of the medical apparatus 112 can be an NFC reader and can communicate with wireless communication devices using an NFC protocol that can be stored in memory 118 for processing by processing resource 117. In one example, the apparatus communication component 116 and wireless communication devices, such as external communication component 246, can communicate at about 13.56 mega-Hertz according to the ISO/IEC 18000-3 international standard for passive RFID for air interface communications. For example, the information can be transmitted in the form of a signal having a frequency of about 13.56 mega-Hertz.

In some examples, an external device 242 can be used to collect information (e.g., medical information), such as a medical status, biological parameters, medical treatment, treatment history, biological parameter history, bone torsion, blood insulin/sugar values, heart pulse rates, etc., or the like from the medical apparatus 112. Further, the external device 242 can be used to collect such information in relation to animals and/or non-human subjects. Further, for example, the current medical status and/or a date and time can be transmitted from the apparatus communication component 116 to the external communication component 246.

In some examples, the medical apparatus 112 and/or the external device 242 can use a passive wireless communication device, such as a short-range communication device (e.g., an NFC tag) that can be as described previously. The NFC tag can include a chip having a non-volatile storage component that stores information, such as a patient identity information, patient medical information, medical device or apparatus information, and/or information about a medical apparatus, such as the model, make, etc., of medical apparatus 112 The NFC tag can include an antenna.

The apparatus communication component 116 can receive information from the NFC tag and/or can transmit information to the NFC tag. In some examples, communications device can include a reader (e.g., an NFC reader), such as a medical apparatus reader.

The memory 118 of the apparatus communications component 116 can include instructions that operate according to an NFC protocol that allows apparatus communications component 116 to communicate with the NFC tag. For example, the apparatus communications component 116 and the NFC tag can communicate using the NFC protocol, such as at about 13.56 mega-Hertz and according to the ISO/IEC 18000-3 international standard.

The apparatus communications component 116 may also communicate with a medical operations center, such as a hospital, medical clinic, etc. For example, apparatus communications component 116 can be wirelessly coupled or hardwired to the medical operations center. In some examples, apparatus communications component 116 can communicate with the medical operations center via WIFI or over the Internet. The apparatus communications component 116 can energize the NFC tag when the antenna 119 associated with the NFC tag is brought within a communication distance of antenna 249, as described previously. The communication distance can be shorter and bring the devices relatively near each other and can provide better security and use less power than previous approaches that use RFID tags.

FIG. 3 illustrates an example environment, including a medical apparatus, an external device, and a server device, in accordance with an embodiment of the present disclosure. As illustrated in FIG. 3, an apparatus communication component 316 can be implanted within and/or be associated with a medical apparatus 312 associated with a patient 305. In one example, the medical apparatus 412 may be a prosthetic device such as a pacemaker. The medical apparatus 312, as illustrated in FIG. 3, can be implanted within a heart, a prosthetic limb, or other structure or organ of the patient 305.

As an example, an apparatus communication component 316 can be within a medical apparatus 312 (e.g., a prosthetic medical device) embedded within a heart, prosthetic, or other organ or structure of a patient 305. As the apparatus communication component 316 of the medical apparatus 312 approaches within a particular proximity of the external communication component 346, communication, indicated by arrow 336-1, can begin and identification and authentication of the external device 333 can occur. The particular proximity, in this example, can refer to a distance of between 50 cm and 100 cm. Embodiments, however, are not limited to a particular proximity. In an example, the particular proximity can depend on a type of antenna (such as antenna 119 in FIG. 1 and antenna 249 in FIG. 2).

The communication, indicated by arrow 336-1, between the apparatus communication component 316 and the external communication component 346 can include an exchange of security data. The security data can include a public identification, a certificate identification, and a public key, as will be described further in association with FIG. 4. Once the security data is verified by each of the medical apparatus 312 and the external device 333, secure medical data can be exchanged between the medical apparatus 312 and the external device 333. This secure medical data can include program updates for the medical apparatus (such as through update system 127 illustrated in FIG. 1), calibration values (such as through calibration system 120), parameter trimming values (such as through parameter trimming system 123), patient data, treatment data, etc. The secure medical data can be exchanged in such a way as to prevent a hacker or nefarious device from intercepting the secure medical data and manipulating the data in order to negatively affect the medical apparatus and ultimately the patient.

The secure medical data received from the medical apparatus 312 to the external device 333 can be transmitted to a server 338 (e.g., a secure remote server) accessible over a network connection 339, e.g., internet connection, or some other network structure, using secure socket layer (SSL) communication. Once connected to the external device 333, the server 338 can connect with the apparatus communication component 316 using the secure protocol that the medical apparatus 312 and the external device 333 used to securely communicate, as will be further described below in association with FIGS. 5-9. In this way, the external device 333 can connect to the medical apparatus 312 and link the medical apparatus 312 to the server 338.

Figure 4:
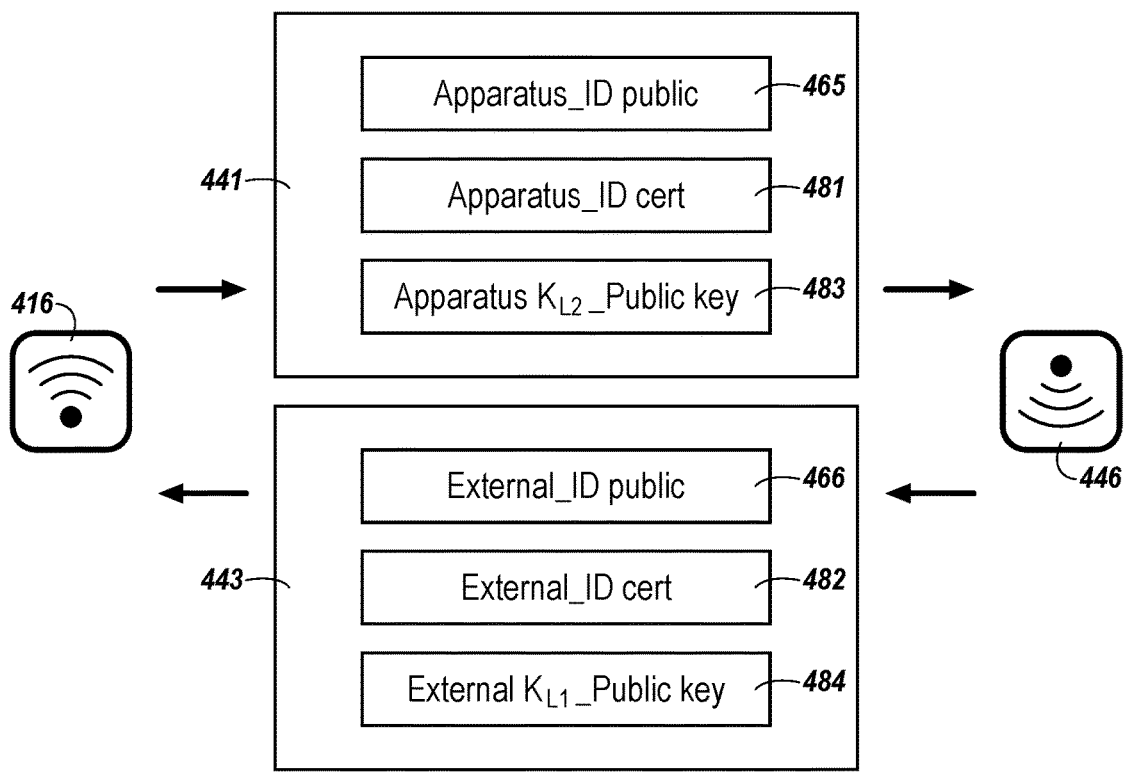
FIG. 4 is an example transmittal of authentication data between an apparatus communication component and an external device in accordance with an embodiment of the present disclosure.

FIG. 4 is an illustration of an exchange of authentication data 441, 443 between an apparatus communication component 416 and an external communication component 446. The portion of authentication data 441 transmitted by the apparatus communication component 416 and received by the external communication component 446 can include an apparatus public identification ("Apparatus_ID public) 465, an apparatus identification certificate ("Apparatus_ID cert") 481, and an apparatus public key ("Apparatus $K_{L2}$_Public key") 483. The apparatus public identification 465 can be used to determine an identity of the apparatus and the apparatus identification certificate 481 can be used to verify that the identity of the apparatus is authenticated. The apparatus public key 483 can be used to encrypt data to be sent to the apparatus communication component 416 in order for the apparatus communication component 416 to decrypt the received data using its own private key, as will be described further in association with FIGS. 5-9.

The portion of authentication data 443 transmitted by the external communication component 446 and received by the apparatus communication component 416 can include an external public identification ("External_ID public") 466, an external identification certificate ("External_ID cert") 482, and an external public key ("External_$K_{L1}$_Public key")

484. The external public identification 466 can be used to determine an identity of the external device sending the security data and the external identification certificate 482 can be used to verify that the identity of the external device is authenticated. The external public key 484 can be used to encrypt data to be sent to the external communication component 446 in order for the external communication component 446 to decrypt the received data using its own private key, as will be described further in association with FIGS. 5-9.

These public keys (apparatus and external) can be used to encrypt data sent to each respective communication component and verify an identity of each and exchange medical data. As an example, as will described further below in association with FIGS. 5-9, the apparatus communication component 416 can encrypt data using the received external public key 484 and send the encrypted data to the external communication component 446. Likewise, the external communication component 446 can encrypt data using the received apparatus public key 483 and send the encrypted data to the apparatus communication component 416. Data, such as medical data sent by the external communication component 446 can include patient verification data, external authentication data (verifying the external device's identity), medical device product data, treatment data associated with a patient using the medical apparatus, patient information data, etc. Confirmation of receipt of the medical data can be sent with a digital signature to verify an identity of the medical apparatus 412 and/or the patient associated with it.

In an example, the apparatus communication component can request additional data to be verified in response to being unable to verify the identity of an external device. By limiting a number of attempts and/or increasing an amount of time between attempts, a nefarious attempt to hack into the system can become more difficult by inserting delays and making the attack last longer.

In an example, data exchanged between the apparatus communication component 416 and the external communication component 446 433 can have a freshness used by the other. As an example, data sent by the apparatus communication component 416 to the external communication component 446 to receipt of the medical data can be altered at each of a particular time frame or for a particular amount of data being sent. This can prevent a hacker from intercepting previously sent data and sending the same data again to result in the same outcome. If the data has been slightly altered but still indicates a same instruction, the hacker may send the identical information at a later point in time and the same instruction would not be carried out due to the recipient expecting the altered data to carry out the same instruction.

The data exchanged between the apparatus communication component 412 and the external communication component 446 can be performed using a number of encryption and/or decryption methods as described below. The securing of the data can insure that nefarious activity is prevented from interfering with the medical data provided to the medical apparatus of the patient and/or interfering with treatment of the patient and/or modification of the medical apparatus. While the exchange of public/private keys are described above in relation to the DICE-RIoT protocol, additional public and/or private keys can be exchanged in association with service information to implement other services and/or protocols.

Figure 5:
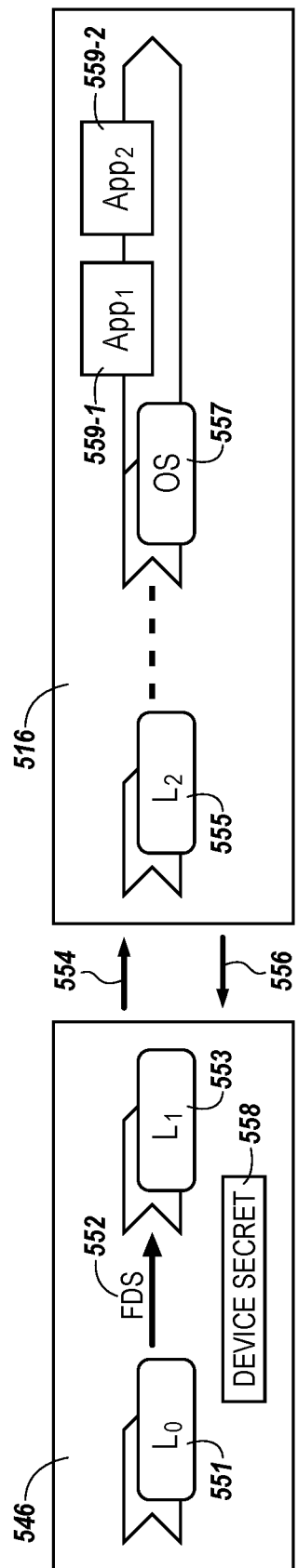
FIG. 5 is a block diagram of an example system including an apparatus communication component and an external communication component in accordance with an embodiment of the present disclosure.

FIG. 5 is a block diagram of an example system including an external communication component 546 and an apparatus communication component 516 in accordance with an embodiment of the present disclosure. As a medical apparatus (e.g., 112 in FIG. 1) comes in close proximity to an external device (e.g., external device 433), the associated apparatus communication component 516 (e.g., 416 in FIG. 4) of the medical apparatus can exchange data with the external communication component 546 of the external device using a sensor (e.g., a radio frequency identification sensor (RFID)).

A computing device can boot in stages using layers, with each layer authenticating and loading a subsequent layer and providing increasingly sophisticated runtime services at each layer. A layer can be served by a prior layer and serve a subsequent layer, thereby creating an interconnected web of the layers that builds upon lower layers and serves higher order layers. As is illustrated in FIG. 5, Layer 0 ("$L_0$") 551 and Layer 1 ("$L_0$") 553 are within the external communication component 546. Layer 0 551 can provide a Firmware Derivative Secret (FDS) key 552 to Layer 1 553. The FDS key 552 can describe the identity of code of Layer 1 553 and other security relevant data. In an example, a particular protocol (such as robust internet of things (RIOT) core protocol) can use the FDS 552 to validate code of Layer 1 553 that it loads. In an example, the particular protocol can include a device identification composition engine (DICE) and/or the RIOT core protocol. As an example, an FDS can include Layer 1 firmware image itself, a manifest that cryptographically identifies authorized Layer 1 firmware, a firmware version number of signed firmware in the context of a secure boot implementation, and/or security-critical configuration settings for the device. A device secret 558 can be used to create the FDS 552 and be stored in memory of the external communication component 546.

The external communication component can transmit data, as illustrated by arrow 554, to the apparatus communication component 516. The transmitted data can include an external identification that is public (e.g., 466 in FIG. 4), a certificate (e.g., an external identification certificate 482), and/or an external public key (e.g., 484). Layer 2 ("$L_2$") 555 of the apparatus communication component 516 can receive the transmitted data execute the data in operations of the operating system ("OS") 557 and on a first application 559-1 and a second application 559-2.

In an example operation, the external communication component 546 can read the device secret 558, hash an identity of Layer 1 553, and perform a calculation including:

$K_{L1}$=KDF[Fs(s), Hash("immutable information")]

where $K_{L1}$ is an external public key, KDF (e.g., KDF defined in the National Institute of Standards and Technology (NIST) Special Publication 800-108) is a key derivation function (i.e., HMAC-SHA256), and Fs(s) is the device secret 558. FDS 552 can be determined by performing:

FDS=HMAC-SHA256 [Fs(s), SHA256("immutable information")]

Likewise, the apparatus communication component 516 can transmit data, as illustrated by arrow 556, including an apparatus identification that is public (e.g., apparatus public identification 465), an apparatus certificate (e.g., a apparatus identification certificate 481), and/or an apparatus public key (e.g., public key 483).

Figure 6:
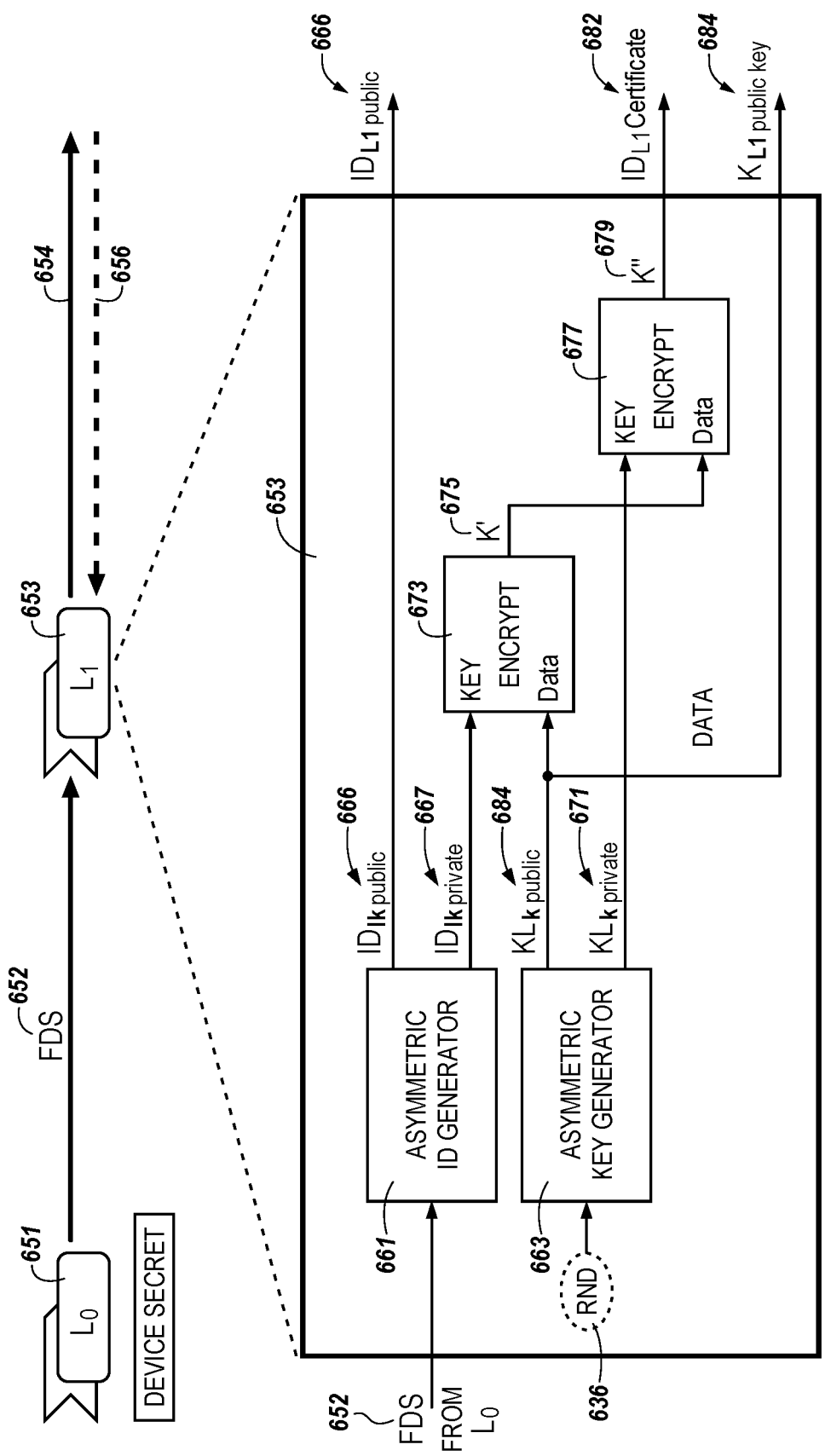
FIG. 6 is a block diagram of an example process to determine a number of parameters in accordance with an embodiment of the present disclosure.

FIG. 6 is a block diagram of an example process to determine a number of parameters in accordance with an embodiment of the present disclosure. FIG. 6 is an example of a determination of the parameters including the apparatus public identification, the apparatus certificate, and the apparatus public key that are then sent, indicated by arrow 654, to Layer 2 (e.g., Layer 2 555) of an apparatus communication component (e.g., 516 in FIG. 5). Layer 0 ("L₀") 651 in FIG. 6 corresponds to Layer 0 551 in FIG. 5 and likewise FDS 652 corresponds to FDS 552, Layer 1 653 corresponds to Layer 1 553, and arrows 654 and 656 correspond to arrows 554 and 556, respectively.

The FDS 652 from Layer 0 651 is sent to Layer 1 653 and used by an asymmetric ID generator 661 to generate a public identification ("ID$_{lk\ public}$") 666 and a private identification 667. In the abbreviated "ID$_{lk\ public}$," the "lk" indicates Layer k (in this example Layer 1), and the "public" indicates that the identification is openly shared. The public identification ("ID$_{L1public}$") 666 is illustrated as shared by the arrow extending to the right and outside of Layer 1 653 of the external communication component. The generated private identification 667 is used as a key input into an encryptor 673. The encryptor 673 can be any processor, computing device, etc. used to encrypt data.

Layer 1 653 of an external communication component can include an asymmetric key generator 663. In at least one example, a random number generator (RND) 636 can optionally input a random number into the asymmetric key generator 663. The asymmetric key generator 663 can generate a public key ("K$_{Lk\ public}$") 684 (referred to as an external public key) and a private key ("K$_{LK\ private}$") 671 (referred to as an external private key) associated with an external communication component such as external communication component 546 in FIG. 5. The external public key 684 can be an input (as "data") into the encryptor 673. The encryptor 673 can generate a result K' 675 using the inputs of the external private identification 667 and the external public key 684. The external private key 671 and the result K' 675 can be input into an additional encryptor 677, resulting in output K" 679. The output K" 679 is the external certificate ("ID$_{L1}$ certificate") 682 transmitted to the Layer 2 (555 of FIG. 5). The external certificate 682 can provide an ability to verify and/or authenticate an origin of data sent from an external device. As an example, data sent from the external communication component can be associated with an identity of the external communication component by verifying the certificate, as will be described further in association with FIG. 8. Further, the external public key ("K$_{L1\ public\ key}$") 684 can be transmitted to Layer 2. Therefore, the public identification 666, the certificate 682, and the external public key 684 of a Layer 1 653 of an external communication component can be transmitted to Layer 2 of an apparatus communication component.

Figure 7:
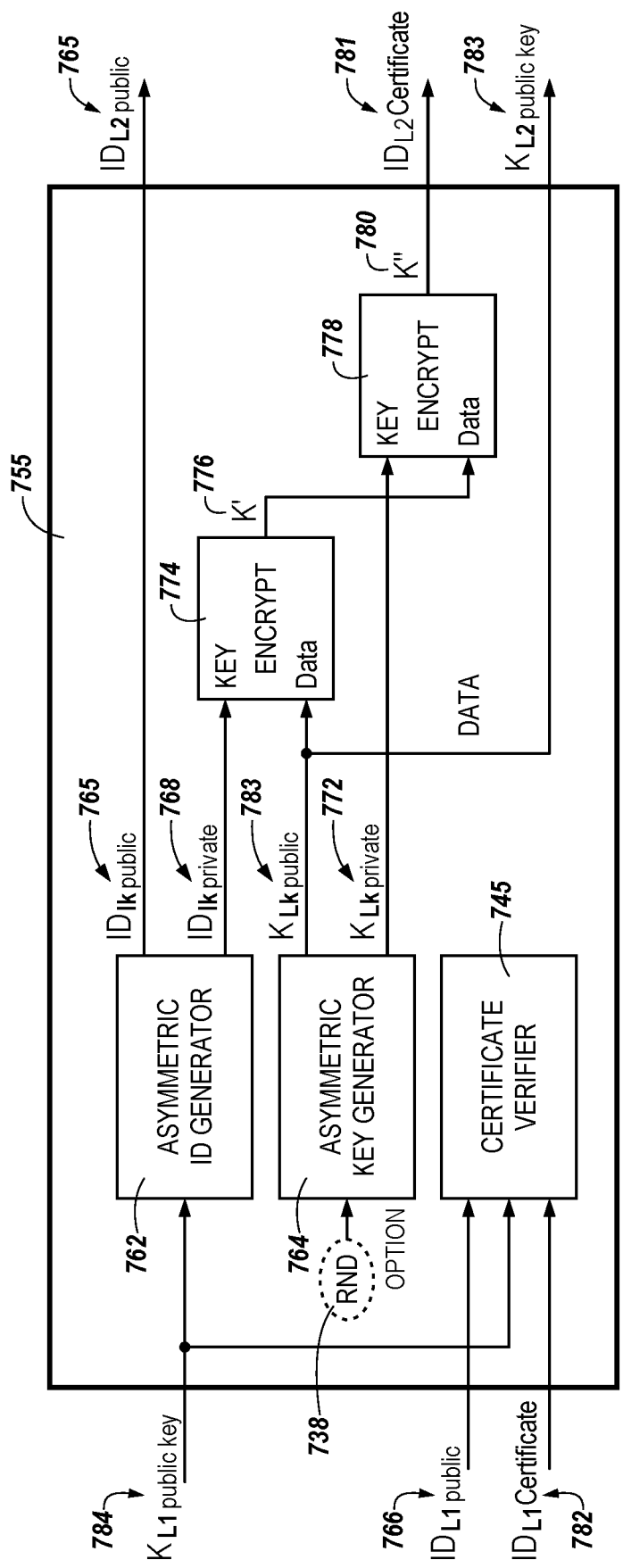
FIG. 7 is a block diagram of an example process to determine a number of parameters in accordance with an embodiment of the present disclosure.

FIG. 7 is a block diagram of an example process to determine a number of parameters in accordance with an embodiment of the present disclosure. FIG. 7 illustrates a Layer 2 755 of an apparatus communication component (e.g., apparatus communication component 516 in FIG. 5) generating an apparatus identification ("ID$_{L2}$ public") 765, an apparatus certificate ("ID$_{L2}$ Certificate") 781, and an apparatus public key ("K$_{L2\ public\ key}$") 783.

The external public key ("K$_{L1\ public\ key}$") 784 transmitted from Layer 1 of the external communication component to Layer 2 755 of an apparatus communication component, as described in FIG. 6, is used by an asymmetric ID generator 762 of the apparatus communication component to generate a public identification ("ID$_{lk\ public}$") 765 and a private identification 768 of the apparatus communication component. In the abbreviated "ID$_{lk\ public}$," the "lk" indicates Layer k (in this example Layer 2), and the "public" indicates that the identification is openly shared. The public identification 765 is illustrated as shared by the arrow extending to the right and outside Layer 2 755. The generated private identification 768 is used as a key input into an encryptor 774.

As shown in FIG. 7, the external certificate 782 and external identification 766, along with the external public key 784, are used by a certificate verifier 745 The certificate verifier 745 can verify the external certificate 782 received from a host (e.g., host 546), and determine, in response to the external certificate 782 being verified or not being verified, whether to accept or discard data received from the host. Further details of verifying an apparatus certificate (e.g., apparatus certificate 881 which can also be used to verify the external certificate 782 by the corresponding device) are described in connection with FIG. 8.

Layer 2 755 of the apparatus communication component can include an asymmetric key generator 764. In at least one example, a random number generator (RND) 638 can optionally input a random number into the asymmetric key generator 764. The asymmetric key generator 764 can generate a public key ("K$_{Lk\ public}$") 783 (referred to as an apparatus public key) and a private key ("K$_{LK\ private}$") 772 (referred to as an apparatus private key) associated with an apparatus communication component such as apparatus communication component 516 in FIG. 5. The apparatus public key 783 can be an input (as "data") into the encryptor 774. The encryptor 774 can generate a result K' 776 using the inputs of the apparatus private identification 768 and the apparatus public key 783. The apparatus private key 772 and the result K' 776 can be input into an additional encryptor 778, resulting in output K" 780. The output K" 780 is the apparatus certificate ("ID$_{L2}$ certificate") 781 transmitted back to the Layer 1 (553 of FIG. 5). The apparatus certificate 781 can provide an ability to verify and/or authenticate an origin of data sent from an apparatus. As an example, data sent from the apparatus communication component can be associated with an identity of the apparatus communication component by verifying the certificate, as will be described further in association with FIG. 8. Further, the apparatus public key ("K$_{L2\ public\ key}$") 783 can be transmitted to Layer 1. Therefore, the public identification 765, the certificate 781, and the apparatus public key 783 of the apparatus communication component can be transmitted to Layer 1 of an external communication component.

In an example, in response to an apparatus communication component receiving a public key from an external communication component, the apparatus communication component can encrypt data to be sent to the external communication component using the external public key. Vice versa, the external communication component can encrypt data to be sent to the apparatus communication component using the apparatus public key. In response to the apparatus communication component receiving data encrypted using the apparatus public key, the apparatus communication component can decrypt the data using its own apparatus private key. Likewise, in response to the external communication component receiving data encrypted using the external public key, the external communication component can decrypt the data using its own external private key. As the apparatus private key is not shared with another device outside the apparatus communication component and the external private key is not shared with another device outside the external communication component, the data sent to the apparatus communication component and the external communication component remains secure.

Figure 8:
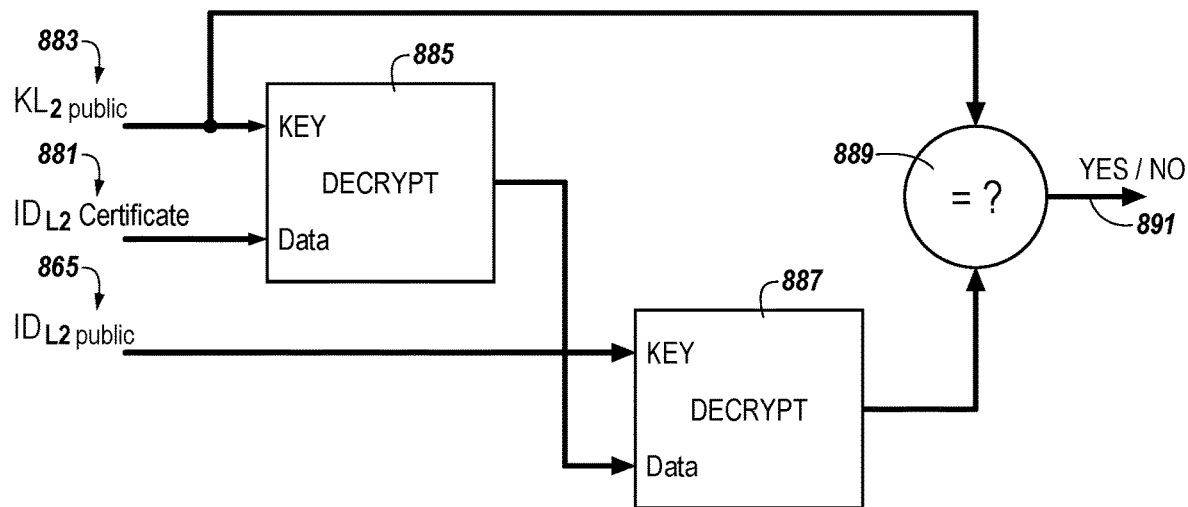
FIG. 8 is a block diagram of an example process to verify a certificate in accordance with an embodiment of the present disclosure.

FIG. 8 is a block diagram of an example process to verify a certificate in accordance with an embodiment of the present disclosure. In the illustrated example of FIG. 8, a public key 883, a certificate 881, and a public identification is provided from an apparatus communication component (e.g., from Layer 2 555 of apparatus communication component 516 in FIG. 5). The data of the certificate 881 and the apparatus public key 883 can be used as inputs into a decryptor 885. The decryptor 885 can be any processor, computing device, etc used to decrypt data. The result of the decryption of the certificate 881 and the apparatus public key 883 can be used as an input into a secondary decryptor 887 along with the public identification, result in an output. The apparatus public key 883 and the output from the decryptor 887 can indicate, as illustrated at 889, whether the certificate is verified, resulting in a yes or no 891 as an output. In response to the certificate being verified, data received from the device being verified can be accepted, decrypted, and processed. In response to the certificate not being verified, data received from the device being verified can be discarded, removed, and/or ignored. In this way, nefarious devices sending nefarious data can be detected and avoided. As an example, a hacker sending data to be processed can be identified and the hacking data not processed.

Figure 9:
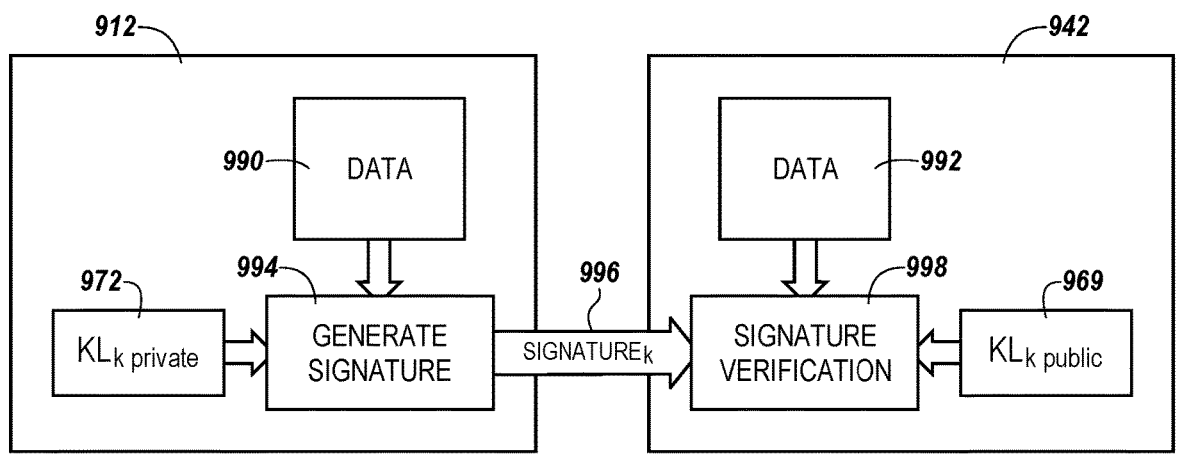
FIG. 9 is a block diagram of an example process to verify a signature in accordance with an embodiment of the present disclosure.

FIG. 9 is a block diagram of an example process to verify a signature in accordance with an embodiment of the present disclosure. In the instance where a device is sending data that may be verified in order to avoid subsequent repudiation, a signature can be generated and sent with data. As an example, a first device may make a request of a second device and once the second device performs the request, the first device may indicate that the first device never made such a request. An anti-repudiation approach, such as using a signature, can avoid repudiation by the first device and insure that the second device can perform the requested task without subsequent difficulty.

A medical apparatus 912 (such as medical apparatus 112 in FIG. 1) can send data 990 to an external device (such as external device 242). The medical apparatus 912 can generate, at 994, a signature 996 using an apparatus private key 972. The signature 996 can be transmitted to the external computing device 942. The external computing device 942 can verify, at 998, using data 992 and the external public key 984 previously received. In this way, signature verification operates by using a private key to encrypt the signature and a public key to decrypt the signature. In this way, the private key used to generate a unique signature can remain private to the device sending the signature while allowing the receiving device to be able to decrypt the signature using the public key of the sending device for verification. This is in contrast to encryption/decryption of the data, which is encrypted by the sending device using the public key of the receiving device and decrypted by the receiving device using the private key of the receiver. In at least one example, the vehicle can verify the digital signature by using an internal cryptography process (e.g., Elliptical Curve Digital signature (ECDSA) or a similar process.

Figure 10:
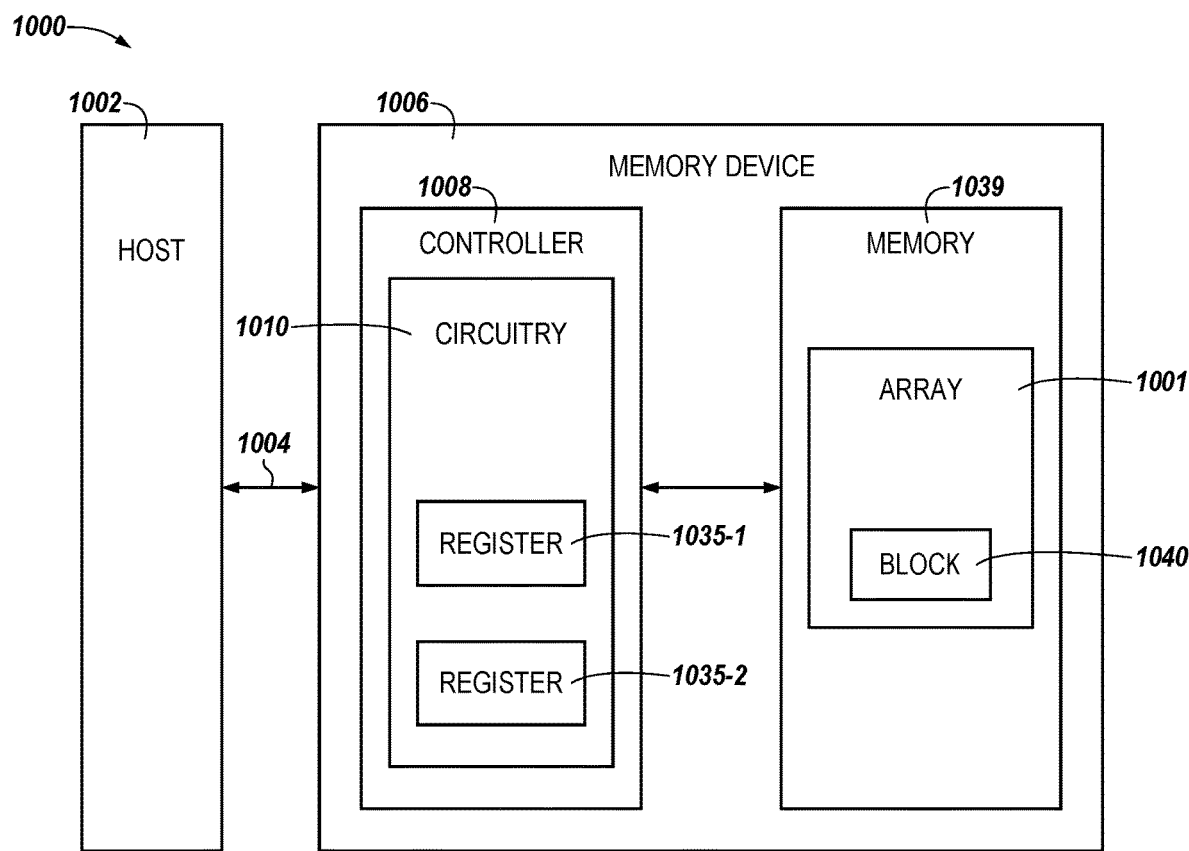
FIG. 10 is a block diagram of a computing system including a host and an apparatus in the form of a memory device in accordance with an embodiment of the present disclosure.

FIG. 10 is a block diagram of a computing system 1000 including a host 1002 and an apparatus in the form of a memory device 1006 in accordance with an embodiment of the present disclosure. As used herein, an "apparatus" can refer to, but is not limited to, any of a variety of structures or combinations of structures, such as a circuit or circuitry, a die or dice, a module or modules, a device or devices, or a system or systems, for example. Further, in an embodiment, computing system 1000 can include a number of memory devices analogous to memory device 1006.

In the embodiment illustrated in FIG. 10, memory device 1006 can include a memory 1039 having a memory array 1001. Memory array 1001 can be a secure array, as will be further described herein. Although one memory array 1001 is illustrated in FIG. 10, memory 1039 can include any number of memory arrays analogous to memory array 1001.

As illustrated in FIG. 10, host 1002 can be coupled to the memory device 1006 via interface 1004. Host 1002 and memory device 1006 can communicate (e.g., send commands and/or data) on interface 1004. Host 1002 and/or memory device 1006 can be, or be part of, a laptop computer, personal computer, digital camera, digital recording and playback device, mobile telephone, PDA, memory card reader, interface hub, or Internet of Things (IoT) enabled device, such as, for instance, an automotive (e.g., vehicular and/or transportation infrastructure) IoT enabled device or a medical (e.g., implantable and/or health monitoring) IoT enabled device, among other host systems, and can include a memory access device (e.g., a processor). One of ordinary skill in the art will appreciate that "a processor" can intend one or more processors, such as a parallel processing system, a number of coprocessors, etc.

Interface 1004 can be in the form of a standardized physical interface. For example, when memory device 1006 is used for information storage in computing system 1000, interface 1004 can be a serial advanced technology attachment (SATA) physical interface, a peripheral component interconnect express (PCIe) physical interface, a universal serial bus (USB) physical interface, or a small computer system interface (SCSI), among other physical connectors and/or interfaces. In general, however, interface 1004 can provide an interface for passing control, address, information (e.g., data), and other signals between memory device 1006 and a host (e.g., host 1002) having compatible receptors for interface 1004.

Memory device 1006 includes controller 1008 to communicate with host 1002 and with memory 1039 (e.g., memory array 1001). For instance, controller 1008 can send commands to perform operations on memory array 1001, including operations to sense (e.g., read), program (e.g., write), move, and/or erase data, among other operations.

Controller 1008 can be included on the same physical device (e.g., the same die) as memory 1039. Alternatively, controller 1008 can be included on a separate physical device that is communicatively coupled to the physical device that includes memory 1039. In an embodiment, components of controller 1008 can be spread across multiple physical devices (e.g., some components on the same die as the memory, and some components on a different die, module, or board) as a distributed controller.

Host 1002 can include a host controller (not shown FIG. 10) to communicate with memory device 1006. The host controller can send commands to memory device 1006 via interface 1004. The host controller can communicate with memory device 1006 and/or the controller 1008 on the memory device 1006 to read, write, and/or erase data, among other operations. Further, in an embodiment, host 1002 can be an IoT enabled device, as previously described herein, having IoT communication capabilities.

Controller 1008 on memory device 1006 and/or the host controller on host 1002 can include control circuitry and/or logic (e.g., hardware and firmware). In an embodiment, controller 1008 on memory device 1006 and/or the host controller on host 1002 can be an application specific integrated circuit (ASIC) coupled to a printed circuit board including a physical interface. Also, memory device 1006 and/or host 1002 can include a buffer of volatile and/or non-volatile memory and a number of registers.

For example, as shown in FIG. 10, memory device can include circuitry 1010. In the embodiment illustrated in FIG. 10, circuitry 1010 is included in controller 1008. However, embodiments of the present disclosure are not so limited. For instance, in an embodiment, circuitry 1010 may be included in (e.g., on the same die as) memory 1039 (e.g., instead of in controller 1008). Circuitry 1010 can comprise, for instance, hardware, firmware, and/or software.

Circuitry 1010 can generate a block 1040 in a block chain for validating (e.g., authenticating and/or attesting) the data stored in memory 1039 (e.g., in memory array 1001). The block 1040 can include a cryptographic hash of (e.g., a link to) the previous block in the block chain, and a cryptographic hash of (e.g., identifying) the data stored in memory array 1001. The block 1040 can also include a header having a timestamp indicating when the block was generated. Further, the block 1040 can have a digital signature associated therewith that indicates the block is included in the block chain.

The cryptographic hash of the data stored in memory array 1001, and/or the cryptographic hash of the previous block in the block chain, can comprise, for instance, a SHA-256 cryptographic hash. Further, the cryptographic hash of the data stored in memory array 1001, and the cryptographic hash of the previous block in the block chain, can each respectively comprise 256 bytes of data.

The cryptographic hash of the data stored in memory array 1001 can be generated (e.g., calculated), for example, by circuitry 1010. In such an example, the cryptographic hash of the data stored can be internally generated by memory device 1006 without having external data moving on interface 1004. As an additional example, the cryptographic hash of the data can be communicated from an external entity. For instance, host 1002 can generate the cryptographic hash of the data stored in memory array 1001, and send the generated cryptographic hash to memory device 1006 (e.g., circuitry 1010 can receive the cryptographic hash of the data stored in memory array 1001 from host 1002).

The digital signature associated with the block 1040 can be generated (e.g., calculated), for example, by circuitry 1010 based on (e.g., responsive to) an external command, such as a command received from host 1002. For instance, the digital signature can be generated using symmetric or asymmetric cryptography. As an additional example, host 1002 can generate the digital signature, and send (e.g. provide) the generated digital signature to memory device 1006 (e.g., circuitry 1010 can receive the digital signature from host 1002).

As shown in FIG. 10, the block 1040, as well as the digital signature associated with block 1040, can be stored in memory array 1001. For example, the block 1040 can be stored in a portion of memory array 1001 that is inaccessible to a user of memory device 1006 and/or host 1002 (e.g., in a "hidden" region of memory array 1001). Storing the block 1040 in memory array 1001 can simplify the storage of the block by, for example, removing the need for software storage management for the block.

In an embodiment, memory array 1001 (e.g., a subset of array 1001, or the whole array 1001) can be a secure array (e.g., an area of memory 1039 to be kept under control). For example, the data stored in memory array 1001 can include sensitive (e.g., non-user) data, such as host firmware and/or code to be executed for sensitive applications. In such an embodiment, a pair of non-volatile registers can be used to define the secure array. For example, in the embodiment illustrated in FIG. 10, circuitry 1010 includes registers 1035-1 and 1035-2 that can be used to define the secure array. For instance, register 1035-1 can define the address (e.g., the starting LBA of the data) of the secure array, and register 1035-2 can define the size (e.g., the ending LBA of the data) of the secure array. Once the secure array has been defined, circuitry 1010 can generate (e.g., calculate) a cryptographic hash associated with the secure array, which may be referred to herein as a golden hash, using authenticated and antireplay protected commands (e.g., so that only memory device 1006 knows the golden hash, and only memory device 1006 is capable of generating and updating it). The golden hash may be stored in inaccessible portion of memory array 1001 (e.g., the same inaccessible portion in which block 1040 is stored), and can be used during the process of validating the data of the secure array, as will be further described herein.

Memory device 1006 (e.g., circuitry 1010) can send, via interface 1004, the block 1040, along with the digital signature associated with block 1040, to host 1002 for validation of the data stored in memory array 1001. For example, circuitry 1010 can sense (e.g., read) the block 1040 stored in memory array 1001, and send the sensed block to host 1002 for validation of the data stored in array 1001, responsive to a powering (e.g., a powering on and/or powering up) of memory device 1006. As such, a validation of the data stored in memory array 1001 can be initiated (e.g., automatically) upon the powering of memory device 1006.

As an additional example, circuitry 1010 can send the block 1040, along with the digital signature associated with block 1040, to host 1002 upon an external entity, such as host 1002, initiating a validation of the data stored in memory array 1001. For instance, host 1002 can send a command to memory device 1006 (e.g., circuitry 1010) to sense the block 1040, and circuitry 1010 can execute the command to sense the block 1040, and send the sensed block to host 1002 for validation of the data stored in array 1001, responsive to receipt of the command.

Upon receiving the block 1040, host 1002 can validate (e.g., determine whether to validate) the data stored in memory array 1001 using the received block. For example, host 1002 can use the cryptographic hash of the previous block in the block chain and the cryptographic hash of the data stored in memory array 1001 to validate the data. Further, host 1002 can validate the digital signature associated with the block 1040 to determine the block is included (e.g., is eligible to be included) in the block chain. As used herein, validating the data stored in memory array 1001 can include, and/or refer to, authenticating and/or attesting that the data is genuine (e.g., is the same as originally programmed), and has not been altered by hacking activity or other unauthorized changes.

In embodiments in which memory array 1001 is a secure array, the golden hash previously described herein may also be used to validate the data stored in memory array 1001. For example, a run-time cryptographic hash can be generated (e.g., calculated), and compared with the golden hash. If the comparison indicates the run-time and golden hashes match, it can be determined that the secure array has not been altered, and therefore the data stored therein is valid. If, however, the comparison indicates the run-time and golden hashes do not match, this may indicate that the data stored in the secure array has been changed (e.g., due to a hacker or a fault in the memory), and this can be reported to host 1002.

After the validation of the data stored in memory array 1001, circuitry 1010 can generate an additional (e.g., the next) block in the block chain for validating the data stored in memory array 1001, in a manner analogous to which the block 1040 was generated. For example, this additional block can include a cryptographic hash of block 1040, which has now become the previous block in the block chain, and a new cryptographic hash of the data stored in memory array 1001. Further, this additional block can include a header having a timestamp indicating when this block was generated, and can have a digital signature associated therewith that indicates this block is included in the block chain. Further, in embodiments in which memory array 1001 is a secure array, an additional (e.g., new) golden hash can be generated.

The additional block, as well as the digital signature associated with the additional block, and the additional golden hash, can be stored in memory array 1001. For example, the additional block can replace block 1040 (e.g., the previous block) in memory array 1001. The additional block, digital signature, and additional golden hash can then be used by host 1002 to validate the data stored in memory array 1001, in a manner analogous to that previously described herein for block 1040. Additional blocks in the block chain can continue to be generated by circuitry 1010, and used by host 1002 to validate the data stored in memory array 1001, in such manner throughout the lifetime of memory device 1006.

The embodiment illustrated in FIG. 10 can include additional circuitry, logic, and/or components not illustrated so as not to obscure embodiments of the present disclosure. For example, memory device 1006 can include address circuitry to latch address signals provided over I/O connectors through I/O circuitry. Address signals can be received and decoded by a row decoder and a column decoder, to access memory array 1001. Further, memory device 1006 can include a main memory, such as, for instance, a DRAM or SDRAM, that is separate from and/or in addition to memory array 1001. An example further illustrating additional circuitry, logic, and/or components of memory device 1006 will be further described herein (e.g., in connection with FIG. 10).

Figure 11:
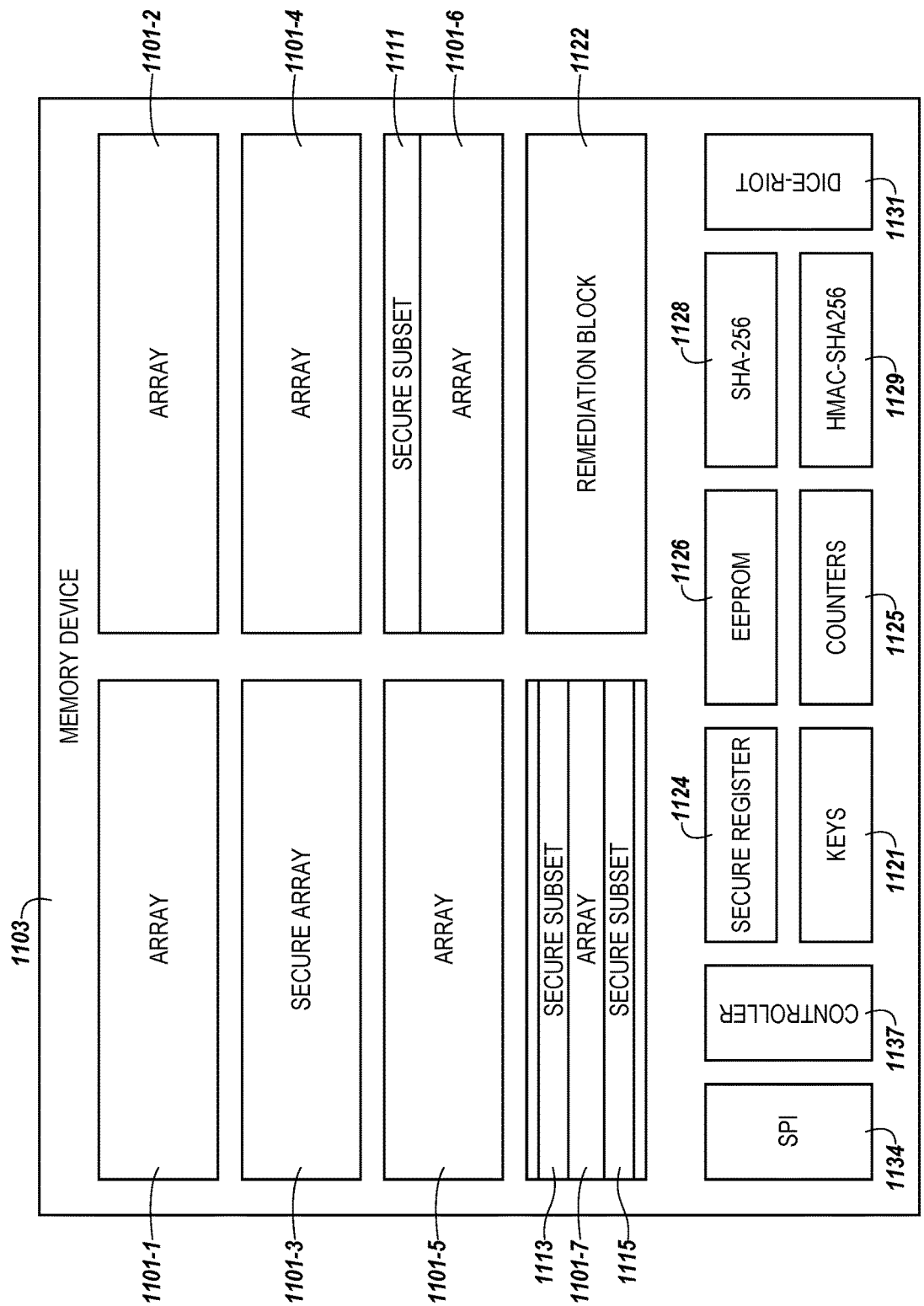
FIG. 11 is a block diagram of an example memory device in accordance with an embodiment of the present disclosure.

FIG. 11 is a block diagram of an example memory device 1103 in accordance with an embodiment of the present disclosure. Memory device 1103 can be, for example, medical apparatus 112, a component of medical apparatus 112, external device 242, or a component of external device 242, as described in association with FIGS. 1 and 2, among other such devices. Further, memory device 1103 can be a same memory device as memory device 1006 described in association with FIG. 10.

As shown in FIG. 11, memory device 1103 can include a number of memory arrays 1101-1 through 1101-7. Further, in the example illustrated in FIG. 11, memory array 1101-3 is a secure array, subset 1111 of memory array 1101-6 comprises a secure array, and subsets 1113 and 1115 of memory array 1101-7 comprise a secure array. Subsets 1111, 1113, and 1115 can each include, for instance, 4 kilobytes of data. However, embodiments of the present disclosure are not limited to a particular number or arrangement of memory arrays or secure arrays.

As shown in FIG. 11, memory device 1103 can include a remediation (e.g., recovery) block 1122. Remediation block 1122 can be used as a source of data in case of errors (e.g., mismatches) that may occur during operation of memory device 1103. Remediation block 1122 may be outside of the area of memory device 1103 that is addressable by a host.

As shown in FIG. 11, memory device 1103 can include a serial peripheral interface (SPI) 1134 and a controller 1137. Memory device 1103 can use SPI 1134 and controller 1137 to communicate with a host and memory arrays 1101-1 through 1101-7.

As shown in FIG. 11, memory device 1103 can include a secure register 1124 for managing the security of memory device 1103. For example, secure register 1124 can configure, and communicate externally, to an application controller. Further, secure register 1124 may be modifiable by an authentication command.

As shown in FIG. 11, memory device 1103 can include keys 1121. For instance, memory device 1103 can include eight different slots to store keys such as root keys, DICE-RIOT keys, and/or other external session keys.

As shown in FIG. 11, memory device 1103 can include an electronically erasable programmable read-only memory (EEPROM) 1126. EEPROM 1126 can provide a secure non-volatile area available for a host, in which individual bytes of data can be erased and programmed.

As shown in FIG. 11, memory device 1103 can include counters (e.g., monotonic counters) 1125. For instance, memory device 1103 can include six different monotonic counters, two of which may be used by memory device 1103 for authenticated commands, and four of which may be used by the host.

As shown in FIG. 11, memory device 1103 can include an SHA-256 cryptographic hash function 1328, and/or an HMAC-SHA256 cryptographic hash function 1129. SHA-256 and/or HMAC-SHA256 cryptographic hash functions 1128 and 1129 can be used by memory device 1103 to generate cryptographic hashes, such as, for instance, the cryptographic hash of a command as previously described herein, and/or a golden hash used to validate data stored in memory arrays 1101-1 through 1101-7. Further, memory device 1103 can support L0 and L1 of DICE-RIOT 1131.

In the preceding detailed description, reference is made to the accompanying drawings that form a part hereof, and in which is shown, by way of illustration, specific examples. In the drawings, like numerals describe substantially similar components throughout the several views. Other examples may be utilized, and structural, logical and/or electrical changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure and should not be taken in a limiting sense.

As used herein, "a," "an," or "a number of" something can refer to one or more of such things. A "plurality" of something intends two or more. As used herein, the term "coupled" may include electrically coupled, directly coupled, and/or directly connected with no intervening elements (e.g., by direct physical contact) or indirectly coupled and/or connected with intervening elements. The term coupled may further include two or more elements that co-operate or interact with each other (e.g., as in a cause and effect relationship).

Although specific examples have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. The scope of one or more examples of the present disclosure should be determined with reference to the appended claims, along with the full range of equivalents to which such claims are entitled.

What is claimed is:

1. An apparatus, comprising:
a processing resource;
memory having instructions executable by the processing resource; and
an apparatus communication component coupled to the processing resource, wherein the apparatus communication component is configured to, in response to receiving data from an external communication component:
receive an external certificate from the external communication component, wherein the external certificate is generated using a firmware derivative secret (FDS) associated with the external communication component; and
verify an identity of the external communication component using the external certificate; and
wherein the apparatus communication component is further configured to:
validate code of a layer associated with the apparatus powering on using a device identification composition engine (DICE) and robust internet of things (RIOT) protocol; and
load the layer associated with the apparatus powering on in the external communication component.

2. The apparatus of claim 1, wherein the apparatus communication component is configured to generate an apparatus private key and an apparatus public key.

3. The apparatus of claim 2, wherein the apparatus communication component is configured to provide the apparatus public key to an external communication component.

4. The apparatus of claim 1, wherein the apparatus communication component is configured to receive the external certificate in response to providing an apparatus public key to the external communication component.

5. The apparatus of claim 1, wherein the apparatus communication component is configured to:
receive data from the external communication component; and
decrypt the received data using a generated apparatus private key prior to verifying the identity of the external communication component.

6. The apparatus of claim 5, wherein the apparatus communication component is configured to, in response to verifying the identity of the external communication component, perform an operation using the received data.

7. The apparatus of claim 6, wherein the apparatus communication component is configured to, in response to performing the operation, provide confirmation of performance of the operation to the external communication component.

8. The apparatus of claim 5, wherein the apparatus communication component is configured to, in response to being unable to verify the identity of the external device, ignore the received data and not perform an operation associated with the received data.

9. The apparatus of claim 1, wherein the apparatus communication component is further configured to, in response to being unable to verify the identity of the external device, request additional data to be verified.

10. The apparatus of claim 1, wherein the apparatus communication component is configured to receive an external digital signature in order to verify the identity of the external device.

11. A method comprising:
receiving, by an external communication component, an apparatus public key and an apparatus certificate from an apparatus communication component, wherein:
the apparatus certificate is generated using a firmware derivative secret (FDS) associated with the apparatus communication component;
a device identification composition engine (DICE) and robust internet of things (RIOT) protocol uses the FDS to validate code of a layer associated with the external communication component powering on; and
the layer associated with the external communication component powering on is loaded in the external communication component; and
verifying an identity of the apparatus communication component using the apparatus certificate.

12. The method of claim 11, further comprising encrypting data using the generated apparatus public key.

13. The method of claim 12, wherein the encrypting is performed using the DICE and RIOT protocol.

14. The method of claim 12, further comprising:
providing the encrypted data to the apparatus communication component; and
receiving data from the apparatus communication component in response to providing the encrypted data to the apparatus communication component.

15. The method of claim 11, further comprising:
generating an external private key and an external public key; and
providing the external public key to the apparatus communication component.

16. The method of claim 11, comprising:
receiving a digital signature from the apparatus communication component; and
verifying the digital signature using the apparatus public key.

17. An apparatus, comprising:
a processing resource;
memory having instructions executable by the processing resource; and
an apparatus communication component coupled to the processing resource, wherein the apparatus communication component is configured to, in response to determining the apparatus communication component is within a particular proximity to an external communication component:
provide an apparatus public key to the external communication component;
receive an external public key and an external certificate from the external communication component, wherein the external certificate is generated using a firmware derivative secret (FDS) associated with the external communication component; and
verify an identity of the external communication component using the external certificate; and
wherein the apparatus communication component is further configured to:

validate code of a layer associated with the apparatus powering on using a device identification composition engine (DICE) and robust internet of things (RIOT) protocol; and load the layer associated with the apparatus powering on in the external communication component.

18. The apparatus of claim 17, wherein the apparatus communication component is configured to:

encrypt data using the external public key; and provide the encrypted data to the external communication component.

19. The apparatus of claim 18, wherein the apparatus communication component is configured to:

receive data from the external communication component in response to providing the encrypted data to the external communication component; and decrypt the received data.

20. The apparatus of claim 19, wherein the apparatus communication component is configured to provide confirmation that the data is executed by the apparatus communication component.

\* \* \* \* \*